United States Patent
Yoshimoto et al.

(10) Patent No.: US 8,163,534 B2
(45) Date of Patent: Apr. 24, 2012

(54) ESTROGENIC SUBSTANCE DEGRADABLE MICROORGANISM AND USE THEREOF

(75) Inventors: Takeshi Yoshimoto, Minato-ku (JP); Fumiko Nagai, Minato-ku (JP); Junji Fujimoto, Minato-ku (JP); Kazumasa Kimura, Minato-ku (JP); Harumi Mizukoshi, Minato-ku (JP); Koichi Watanabe, Minato-ku (JP); Takashi Makino, Minato-ku (JP); Hiroshi Omura, Minato-ku (JP); Hideyuki Saino, Tsukuba (JP)

(73) Assignees: Kabushiki Kaisha Yakult Honsha, Tokyo (JP); Japan as represented by Director-General of the Ministry of Land, Infrastructure and Transport, National Institute for Land and Infrastructure Management, Tsukuba-shi (JP)

( * ) Notice: Subject to any disclaimer, the term of this patent is extended or adjusted under 35 U.S.C. 154(b) by 1175 days.

(21) Appl. No.: 11/816,865

(22) PCT Filed: Feb. 23, 2006

(86) PCT No.: PCT/JP2006/303271
§ 371 (c)(1),
(2), (4) Date: Aug. 22, 2007

(87) PCT Pub. No.: WO2006/090780
PCT Pub. Date: Aug. 31, 2006

(65) Prior Publication Data
US 2009/0029442 A1 Jan. 29, 2009

(30) Foreign Application Priority Data
Feb. 23, 2005 (JP) .................................. 2005-046392

(51) Int. Cl.
| C02F 3/34 | (2006.01) |
| C12M 1/00 | (2006.01) |
| C12N 1/00 | (2006.01) |
| C12N 1/12 | (2006.01) |
| C12N 1/20 | (2006.01) |

(52) U.S. Cl. .................. 435/255.3; 435/243; 435/252.1; 435/262; 435/283.1; 435/822

(58) Field of Classification Search ........................ None
See application file for complete search history.

(56) References Cited

U.S. PATENT DOCUMENTS
5,591,634 A * 1/1997 Higa ............................ 435/262

FOREIGN PATENT DOCUMENTS

| JP | 11 341978 | 12/1999 |
| JP | 2001 333767 | 12/2001 |
| JP | 2003 52356 | 2/2003 |
| JP | 2003 274927 | 9/2003 |
| JP | 2004 49129 | 2/2004 |
| JP | 2004 65008 | 3/2004 |
| JP | 2004 261123 | 9/2004 |
| JP | 2004 321052 | 11/2004 |

OTHER PUBLICATIONS

R. G. Coombe, et al., "Mechanisms of Steroid Oxidation by Microorganisms", The Journal of Biological Chemistry, vol. 241, No. 7, p. 1587, 1966.
Katsuhiko Fujii, et al., "Degradation of 17 Beta-Estradiol by a Gram-Negative Bacterium Isolated From Activated Sludge in a Sewage Treatment Plant in Tokyo, Japan", Applied and Environmental Microbiology, vol. 68, No. 4, pp. 2057-2060, 2002.
Kampfer et al, Int. J. Syst. Bacteriol., (1999), vol. 49, pp. 887-897.
Rossello-Mora et al, FEMS Micro. Letts., (1993), vol. 114, pp. 129-134.
Coenye et al, Int. J. Syst. and Evol. Micro., (2000), vol. 50, pp. 887-899.
Middlehoven et al, FEMS Yeast Research, (2001), vol. 1, pp. 15-22.
Takeshi Yoshimoto, et al., "Degradation of Estrogens by *Rhodococcus zopfii* and *Rhodococcus equi* Isolates from Activated Sludge in Wastewater Treatment Plants", Applied and Environmental Microbiology, vol. 70, No. 9, XP002524471, Sep. 2004, pp. 5283-5289.
Jianghong Shi, et al., "Biodegradation of natural and synthetic estrogens by nitrifying activated sludge and ammonia-oxidizing bacterium *Nitrosomonas europaea*", Water Research, Elsevier, vol. 38, No. 9, XP004508322, May 1, 2004, pp. 2322-2329.
Katsuhiko Fuji!, et al., "*Novoshingobium tardaugens* sp. nov., an oestradiol-degrading bacterium isolated from activated sludge of a sewage treatment plant in Tokyo", International Journal of Systematic and Evolutionary Microbiology, Society for General Microbiology, vol. 53, No. 1, XP009032387, Jan. 1, 2003, pp. 47-52.
Cläre Hörhold, et al., "Über den Abbau von Steroiden durch Mikroorganismen", "[The breakdown of steroids by microorganisms]", Zeitschrift füAllgemeine Mikrobiologie, vol. 9, No. 3, XP009115572, 1969, pp. 235-246.

* cited by examiner

*Primary Examiner* — Debbie K Ware
(74) *Attorney, Agent, or Firm* — Oblon, Spivak, McClelland, Maier & Neustadt, L.L.P.

(57) ABSTRACT

A microorganism capable of degrading an estrogenic substance contained in wastewater and the like; a method for the simple and effective degradation of an estrogenic substance contained in domestic wastewater, wastewater discharged from a livestock farm, or the like by using the microorganism; and an apparatus for achieving the degradation are provided. An estrogenic substance-degrading microorganism which belongs to the genus *Pseudaminobacter, Gordonia, Nocardia, Zoogloea, Pandoraea, Cryptococcus* or *Trichosporon* and has an ability to degrade an estrogenic substance; a method for the degration of an estrogenic substance by using the microorganism; and an apparatus for achieving the degradation are provided.

11 Claims, 4 Drawing Sheets

```
                          SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agagtttgat cmtggctcag                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggaggtga tccarccgca                                                      20

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```

```
tatctggttg atcctgccag t                                              21
```

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
ctacggaaac cttgttacga c                                              21
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
caggagtgcc agcagccgcg g                                              21
```

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
caagcggtgg agcatgtgg                                                 19
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
caggagcaac gagcgcaacc c                                              21
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

```
accgcggctg ctggc                                                     15
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ggactaccag ggtatctaat                                                20
```

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agggttgcgc tcgttg                                                    16

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccggagaggg agcctgag                                                  18

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgcgcgcc tgctgcctt                                                 19

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agccgcggta attccagc                                                  18

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgtcctattc tattattcca tgc                                            23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aagaacgaaa gttaggggat c                                              21

```
<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctttccccgt gttgagtcaa                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aggtctgtga tgcccttaga                                              20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgcttactag gaattcctcg tt                                           22
```

ESTROGENIC SUBSTANCE DEGRADABLE MICROORGANISM AND USE THEREOF

This Application is a filing under 35 U.S.C. 371, of International Application No. PCT/JP2006/303271, filed Feb. 23, 2006; and which claims priority to Japanese Application No. 2005-046392, filed Feb. 23, 2005. These applications are hereby incorporated by reference and relied upon in their entirety.

TECHNICAL FIELD

The present invention relates to an estrogenic substance-degrading microorganism and use thereof, and, more particularly, to a microorganism capable of degrading an estrogenic substance contained in domestic wastewater, wastewater discharged from a livestock farm, and the like, a method for biologically degrading an estrogenic substance using the microorganism, and an apparatus for achieving the degradation.

BACKGROUND ART

Endocrine disruptors which disrupt the endocrine system in a living body have been understood to be a serious social problem since T. Colborn published "Our Stolen Future" in 1996. The endocrine system in a body is a system which maintains and regulates generation of an organism, development of sexual organs, and functions of various organs in a living body caused by actions of an androgen, an estrogen, a thyroid hormone, an adrenal cortical hormone, and the like. Endocrine-disrupting chemicals are a group of substances which disrupt the endocrine system in a body. A large amount of endocrine disruptors are discharged into the world of nature by various human activities and the like and cause a great deal of abnormal growth in wildlife.

Along with estrogenic substances, organochlorine compounds such as pesticides, antibacterial agents, and herbicides and industrial chemicals such as bisphenol A and nonylphenol are known as endocrine-disrupting chemicals. Among these, the use of industrial chemicals has been strictly regulated by The Water Pollution Control Law and other pollution regulations because of their toxic property. The amount of these chemicals discharged into the environment is now decreasing. However, the amount of estrogenic substances such as 17β-estradiol, estrone, and estriol contained in human and animal urine discharged into the environment is increasing along with the population growth. Abnormal feminization of wildlife has been confirmed in rivers and lakes into which large amounts of domestic wastewaters flow from urban area ("The Feminization of Nature" written by Deborah Cadbury, edited by Taisen Iguchi, Shueisha, 1998). This suggests that incapacity to fertilize may unbalance ecosystems.

17β-estradiol shown by the following formula (I) is a steroid hormone secreted from the ovarian follicle and is the most physiologically active substance among the estrogenic substances. Its secretion is controlled by follicle-stimulating hormones and luteinizing hormones in the pituitary gland. 17β-estradiol is used as a medicine for treating amenorrhea, menstrual disorder, dysmenorrhea, hypoplasia uteri, postmenopausal syndrome, and the like.

Estrone shown by the following formula (II) is a type of estrogen which is a metabolite of 17β-estradiol. Estrone which has a strong estrogenic activity appears in urine and is discharged from the body. Estrone is used as a hormonal agent for treating sexual dysfunction in women, postmenopausal syndrome, prostate cancer in men, and the like.

Estriol shown by the following formula (III) is an estrogen which is a metabolite of 17β-estradiol in a body which is formed through estrone and discharged in the urine. Estriol has an estrus effect.

As described above, estrogenic substances are used as human medications. They are contained in the urine and discharged from the body together with the urine. These substances are also administered to farm animals and are thus discharged into the environment from livestock farms. Because wildlife and fishes in rivers and lakes are contaminated with these estrogenic substances, it is necessary to decrease the estrogenic substances contained in wastewater before discharge into a river or the like, for example, in wastewater treatment facilities.

There are three types of wastewater treating methods currently used in wastewater treatment facilities: physical treatment, chemical treatment, and biological treatment. The physical treatment includes centrifugation, filtration, pressurized flotation separation, adsorption, and the like. Chemical treatment, specifically, is detoxification of toxic substances by adding chemicals and the like, electrodialysis, ion exchange, and the like. On the other hand, biological treatment is a treatment using microorganisms to degrade and remove organic substances in wastewater and is effective for treating substances difficult to treat physically or chemically.

Biological treatment has been popularly used in many wastewater treatment facilities in recent years. Biological treatment, in general, has three steps: a preliminary treatment, a biological oxidation treatment, and a sludge treatment. The preliminary treatment comprises treatments using a screen, a sand basin, a settling basin, a floating bath, and the like. These devices remove solid materials and inorganic floating materials having a large particles size in wastewater, and are useful in reducing the load of organic substances in biological oxidation treatment facilities.

Biological oxidation treatment, on the other hand, uses microorganisms. As the method of using microorganisms, a method of causing microorganisms to adhere to the surface of a solid support and growing the microorganisms on the surface, and a method of suspending microbial groups in a liquid can be given. The former method is usually carried out using a fixed bed apparatus of a trickling filter process, while a fluidized bed apparatus of an activated sludge process is used for the latter method.

Among these, in the method of treating wastewater using a fixed bed apparatus, a bonding immobilization method, an enclosing immobilization method, and the like are employed to immobilize microorganisms. The bonding immobilization method is a method of causing microorganisms to adhere to an insoluble carrier by a covalent bond, ionic bond, hydrogen bond, physical adsorption, or the like. The enclosing immobilization method is a method of enclosing the microorganisms in a polymer gel produced by polymerization or association of a low molecular compound or by changing the state of a polymer compound from a soluble state to an insoluble state. A ceramic carrier, a cellulose carrier, particulate activated carbon, and the like are used as a material in the former method, while polyvinyl alcohol (PVA), carageenan, and the like are used as a material in the latter method.

Since the activated sludge treatment, trickling filter treatment, and the like are very excellent methods of reducing pollution substances in wastewater, various biological approaches of degrading endocrine disruptors has been actively undertaken in recent years. Some efforts include improvement of the treating efficiency and employment of a more stringent standard for screening and selecting microorganisms that can degrade endocrine disruptors of which the treatment is difficult. Until now, microorganisms belonging to the genus *Sphingomonas* capable of degrading nonylphenol (Patent document 1), microorganisms belonging to the genus *Fusarium* capable of degrading dioxine (Patent document 2), microorganisms belonging to the genus *Fusarium* capable of degrading ethynylestradiol which is a synthetic estrogen (Patent document 3), and the like have been reported. The applicant of the present invention has reported microorganisms belonging to the genus *Rhodococcus* or *Sphingomonas* which can degrade 17β-estradiol and the like (Patent document 4).

However, few microorganisms capable of quickly and effectively degrading estrogenic substances which are particularly difficult to degrade by treatment with microorganisms have been discovered. A microorganism having higher degrading capability is demanded.

The applicant of the present invention has reported microorganisms belonging to the genus *Rhodococcus* or *Sphingomonas* which can degrade 17β-estradiol and the like. However, although these estrogen degrading bacteria exhibit good degrading capabilities in circumstances in which a comparatively low-concentration estrogen continuously flows, their effects are not sufficient in circumstances that allows a high-concentration estrogen to primarily flow.

[Patent document 1] Japanese Patent Application Laid-open No. 2001-333767
[Patent document 2] Japanese Patent Application Laid-open No. 11-341978
[Patent document 3] Japanese Patent Application Laid-open No. 2003-52356
[Patent document 4] Japanese Patent Application Laid-open No. 2004-65008

DISCLOSURE OF THE INVENTION

Problems to be Solved by the Invention

The present invention has been completed in view of such a situation and has an object of providing an estrogenic substance degrading microorganism, a method for simply and effectively degrading an estrogenic substance contained in domestic wastewater, wastewater discharged from a livestock farm, or the like by using the microorganism, and an apparatus for achieving the degradation.

Means for Solving the Problems

As a result of extensive studies, the inventors of the present invention have discovered microorganisms capable of effectively degrading estrogenic substances by using the selection method which is discussed later. The inventors have further found that the estrogenic substance contained in wastewater or the like can be simply and effectively degraded using the microorganism. These findings have led to the completion of the present invention.

Specifically, the present invention provides estrogenic substance-degrading microorganisms which belong to the genus *Pseudaminobacter, Gordonia, Nocardia, Zoogloea, Pandoraea, Cryptococcus*, or *Trichosporon*.

The present invention also provides a method for biologically degrading an estrogenic substance using one of the above mentioned microorganisms.

The present invention further provides an apparatus for degrading an estrogenic substance comprising a means for supporting the above-mentioned estrogenic substance-degrading microorganism and a means for causing the microorganism to come in contact with wastewater or soil.

Furthermore, the present invention is used for degradation of an estrogenic substance by the above mentioned estrogenic substance-degrading microorganisms.

Effect of the Invention

The estrogenic substance-degrading microorganism of the present invention has the capability of degrading estrogenic substances such as 17β-estradiol, estrone, or estriol.

Therefore, the estrogenic substances in wastewater and soil polluted with the estrogenic substances can be degraded by using the method and apparatus for degrading estrogenic substances in which the above-mentioned microorganism is used, whereby the environment can be improved.

BEST MODE FOR CARRYING OUT THE INVENTION

The estrogenic substance-degrading microorganism of the present invention (hereinafter referred to as "microorganism of the present invention") has the capability of degrading estrogenic substances in a living body, such as 17β-estradiol, estrone, and estriol which are respectively shown by the above formulas (I) to (III), or their metabolites (hereinafter referred to collectively as "estrogenic substances"). These estrogenic substances cannot be removed by a common biological oxidation treatment and can be chemically treated only with difficulty due to their stable chemical structure.

As the microorganism of the present invention having these characteristics, microorganisms belonging to the genus *Pseudaminobacter, Gordonia, Nocardia, Zoogloea, Pandoraea, Cryptococcus*, or *Trichosporon* can be given. More specifically, one or more microorganisms belonging to the following Group A can be given.

<Group A>
*Pseudaminobacter salicylatoxidans*
*Gordonia terrae*
*Gordonia rubropertinctus*
*Gordonia amarae*
*Nocardia asteroides*
*Zoogloea* sp.
*Pandoraea pnomenusa*
*Cryptococcus* sp.
*Trichosporon loubieri*

These microorganisms of the present invention can be obtained from various microorganisms which exist in activated sludge and return sludge in sewage disposal plants and the like by multistage screening using an estrogenic substance.

Specifically, in order to obtain the microorganism of the present invention from various microorganisms which exist in activated sludge in sewage disposal plants and the like, microorganisms contained in activated sludge are cultured by enrichment culture using an estrogenic substance to separate microorganisms degrading estrogenic substances from microorganisms which do not degrade estrogenic substances.

The enrichment culture is preferably carried out using a culture broth containing sludge such as activated sludge and return sludge, and MDG culture medium, for example, which contains an estrogenic substance and has a composition of the following Table 1 (Modified DOMINIC & GRAHAM's medium; compounds listed in Table 2 are used as trace elements). It is desirable to culture microorganisms by vigorously shaking a test tube or the like at a temperature of about 28° C., for example, for one week per each generation. Culturing of about five generations is preferable.

TABLE 1

| MDG Medium | Unit: (wt/vol)% |
|---|---|
| $K_2HPO_4$ (g/L) | 3.5 |
| $KH_2PO_4$ | 1.5 |
| $(NH_4)_2SO_4$ | 0.5 |
| NaCl | 0.5 |
| $MgSO_4 \cdot 7H_2O$ | 0.15 |
| Trace elements (mL/L) | 1.0 |
| Yeast extract | 0.005 or 0 |
| pH | 6.0 or 7.0 |

TABLE 2

| Trace element | Unit: g/L |
|---|---|
| $NaHCO_3 \cdot 10H_2O$ | 2.0 |
| $MnSO_4 \cdot 4H_2O$ | 0.3 |
| $ZnSO_4 \cdot 7H_2O$ | 0.2 |
| $(NH_4)Mo_7O_{24} \cdot 4H_2O$ | 0.02 |

TABLE 2-continued

| Trace element | Unit: g/L |
|---|---|
| $CuSO_4 \cdot 5H_2O$ | 0.1 |
| $CoCl_2 \cdot 6H_2O$ | 0.5 |
| $CaCl_2 \cdot 2H_2O$ | 0.05 |
| $FeSO_4 \cdot 7H_2O$ | 0.5 |

Next, whether or not the estrogenic substances have been degraded in the enrichment culture solution obtained above is examined and confirmed using a thin-layer chromatography (TLC) and the like, and the enrichment culture solutions in which the estrogenic substances have been degraded are selected.

Microorganisms contained in the enrichment culture solution selected in this manner are isolated using a common culture medium used for separation of microorganisms, for example, a commercially available culture medium such as ISP culture medium, $R_2A$ culture medium, and YM culture medium.

Each of the microorganisms isolated is further cultured in a culture medium containing estrogenic substances, and microorganisms with high estrogenic substance-degrading capability can be screened by measuring the amount of the estrogenic substances remaining in the culture medium after culturing, using, for example, a thin-layer chromatography (TLC), gas chromatography, or the like. A microorganism with a high estrogenic substance-degrading capability can be obtained by repeating this screening operation several times.

When $10^7$ to $10^8$ cells/L of the microorganism of the present invention obtained in this manner are caused to act on sludge, sewage, a culture medium, or the like containing estrogenic substances at a concentration of 100 mg/L, the microorganism can degrade 65% or more, and preferably 80% or more of the estrogenic substances contained in the culture medium after five hours. The microorganism of the present invention can particularly degrade 90% or more, and more preferably 99% or more, of 17β-estradiol among estrogenic substances in eight hours. The temperature at which the microorganism of the present invention is caused to act is 25 to 30° C., and preferably 27 to 28° C.

Specifically, the following nine microorganism strains were obtained as estrogenic substance-degrading microorganisms by the above-mentioned screening method from the activated sludge or return sludge of Fushimi Wastewater Treatment Plant (Kyoto-shi, Kyoto), Tarumi Wastewater Treatment Plant (Kobe-shi, Hyogo), Tamagawa-joryu Treatment Plant (Akishima-shi, Tokyo), Morigasaki Treatment Center (Ota-ku, Tokyo), Northern Second Wastewater Treatment Plant (Yokohama-shi, Kanagawa), Todoroki Environment Center (Kawasaki-shi, Kanagawa), and Tachikawa-Fujimi Treatment Plant (Tachikawa-shi, Tokyo). These microorganism strains were identified by the molecular evolution system analysis described by Carl R. Woese, Bacterial Evolution., Microbiological Reviews., 51: 221-271 (1987) and E. Stackebrandt and B. M. Goebel, Taxonomic Note, A Place for DNA-DNA Reassociation and 16S rRNA Sequence Analysis in the Present Species Definition in Bacteriology., International Journal of Systematic Bacteriology, 44, (4), 846-849 (1994), using the 16S rDNA sequence of the microorganisms.

*Pseudaminobacter salicylatoxidans* TAA-I3 strain (FERM BP-10519)
*Gordonia terrae* TAI-I5 strain (FERM BP-10521)
*Gordonia rubropertinctus* TAJ-I4 strain (FERM BP-10520)
*Gordonia amarae* TAJ-I6 strain (FERM P-20024)

*Nocardia asteroides* TAJ-I7 strain (FERM BP-10522)
*Zoogloea* sp. TMJ-I1 strain (FERM BP-10523)
*Pandoraea pnomenusa* TMM-Y4 strain (FERM BP-10524)
*Cryptococcus* sp. TMN-Y2 strain (FERM BP-10525)
*Trichosporon loubieri* FF-Y2 strain (FERM BP-10526)

Among these microorganisms, *Pseudaminobacter salicylatoxidans* TAA-I3 strain, *Gordonia terrae* TAI-I5 strain, *Gordonia rubropertinctus* TAJ-I4 strain, *Nocardia asteroides* TAJ-I7 strain, *Zoogloea* sp. TMJ-I1 strain, *Pandoraea pnomenusa* TMM-Y4 strain, *Cryptococcus* sp. TMN-Y2 strain, and *Trichosporon loubieri* FF-Y2 strain were internationally deposited with the Independent Administrative Agency, National Institute of Advanced Industrial Science and Technology, International Patent Organism Depositry Center (Address: Chuo No. 6, 1-1, Higashi 1-Chome, Tsukuba-shi, Ibaraki, 305-8566, Japan) with the above-described depository number on Apr. 26, 2004.

*Gordonia amarae* TAJ-I6 strain was domestically deposited with the Independent Administrative Agency, National Institute of Advanced Industrial Science and Technology, International Patent Organism Depositry Center (Address: Chuo No. 6, 1-1, Higashi 1-Chome, Tsukuba-shi, Ibaraki, 305-8566, Japan) with the above-described depository number on Apr. 26, 2004.

Microbiological characteristics of the *Pseudaminobacter salicylatoxidans* TAA-I3 strain among the above microorganisms were examined and found to be as follows.
Form: is strictly aerobic and aplanetic, grows in the form of hyphae, forms a yellow colony in many cases, and is included in Proteobacteria α-subdivision of gram negative bacteria.
Physiological characteristics: is positive to oxidase and catalase.
Growth range: grows at a temperature of 20 to 40° C., but does not grow when incubated at 10° C. or 45° C. for seven days.
Utilization of saccharides: aerobically utilizes D-glucose, D-mannitol, dulcitol, and melibiose and exhibits an anabolic effect on D-glucose, D-maltose, D-ribose, D-xylose, and the like.

These characteristics are the same as the characteristics of *Pseudaminobacter* sp., which includes *Pseudaminobacter salicylatoxidans*, reported by P. Kampfer, Description of *Pseudoaminobacter* gen. Nov. with two new species, *Pseudaminobacter salicylatoxidans* sp. Nov. and *pseudaminobacter defluvii* sp. Nov., International Journal of Systematic Bacteriology, 49:887-897 (1999).

Microbiological characteristics of the *Gordonia* terrae TAI-I5 strain, Gordonia rubropertinctus TAJ-I4 strain, and *Gordonia* amarae TAJ-I6 strain among the above microorganisms were examined and found to be as follows.
Form: are strictly aerobic, aplanetic, and weakly acid-fast short bacillus or pseudococcus. Only *Gordonia amarae* exhibits hypha-like growth and produces a slight amount of aerial hyphae that can be observed by a microscope. Form red and yellow colonies in many cases and can be separated from environments such as soil and activated sludge, and are included in *Corynebacterium* of High-GC gram positive coccus.
Physiological characteristics: The cell-wall peptidoglycan is A1γ-type, many of which are glycolyl-types and include arabinose and galactose. The basic component of a respiratory chain quinone is MK-9 ($H_2$). The cell fatty acid is a linear mono-unsaturated-type and contains 10Me-18:0. The content of odd number acids varies according to species. As phospholipids, in addition to PE, DPG, PG, PI, and PIMs are detected. There are also some glycolipids.
Growth range: Optimum growth temperature is 28 to 37° C.

These characteristics are the same as the characteristics of *Gordonia* sp. including *Gordonia terrae*, *Gordonia rubropertinctus*, and *Gordonia amarae* described in "Classification and Identification of *Actinomyces*" Business Center for Academic Societies Japan, edited by The Society for *Actinomyces* Japan: 183-184 (2001). Microbiological characteristics of the Nocardia asteroides TAJ-I7 strain among the above microorganisms were examined and found to be as follows.
Form: is strictly aerobic and aplanetic, grows in the form of hypha, is weakly acid-fast, and does not form spores. Elongated hyphae are disrupted into short bacillus- or pseudococcus-like bacteria by lapse of incubation time. Exhibits most marked hypha-like growth among microorganisms in the mycolic acid-containing bacillus group, forms brown colonies in many cases, and is included in the *Corynebacterium* group of High-GC gram positive coccus.
Physiological characteristics: is positive to catalase, but negative to oxidase. The cell-wall peptidoglycan is A1γ-type, many of which are glycolyl-types and include arabinose and galactose. The cell fatty acid is a linear mono-unsaturated-type and contains 16:0, 18:0, 18:1, and 10Me-18:0. As phospholipids, in addition to PE, DPG, PG, PI, and PIMs are detected. There are also some glycolipids.
Growth range: Optimum growth temperature is 20 to 37° C.

These characteristics are the same as the characteristics of *Nocardia* sp. including *Nocardia asteroides*, described in "Classification and Identification of *Actinomyces*" Business Center for Academic Societies Japan, edited by The Society for *Actinomyces* Japan: 183-184 (2001).

Microbiological characteristics of the *Zoogloea* sp. TMJ-I1 strain among the above microorganisms were examined and found to be as follows.
Form: is strictly aerobic and aplanetic, grows in the form of hyphae, forms white to pale yellow colonies in many cases, is included in Proteobacteria β-subdivision of gram negative bacteria, and exists in sludge by forming flocks.
Physiological characteristics: possesses urease, oxidase, and gelatinase activities.
Growth range: Optimum growth temperature is 20 to 37° C.

These characteristics are the same as the characteristics of *Zoogloea* sp. described in published documents (Rossello-Mora, R., Ludwig, W. and Schleifer, K. H.: *Zoogloea ramigera*, a phylogenetically diverse species, FEMS Microbiol. Lett. 114, 129-134 (1993) and R. G. E. Murray: BERGY'S MANUAL of Systematic Bacteriology, Volume 4, 214-219 (1992)).

Microbiological characteristics of the *Pandoraea pnomenusa* TMM-Y4 strain among the above microorganisms were examined and found to be as follows.
Form: is strictly aerobic and aplanetic, does not grow in the form of hyphae, is adherent, forms white to yellow colonies in many cases, and is included in Proteobacteria β-subdivision of gram negative bacteria.
Physiological characteristics: is positive to catalase, has alkaline phosphatase activity, and exhibits an anabolic effect on phenylacetate. The cell fatty acid is cyclic and contains 16:0 and 17:0.
Growth range: Optimum growth temperature is 42° C.

These characteristics are the same as the characteristics of *Pandraea* sp., which includes *Pandoarea pnomenusa*, reported in published documents (T. Coenye, Description of *Pandoraea* gen. Nov. with *Pandoraea apista* sp. Nov., *Pandoraea pulmonicola* sp. Nov., *Pandoraea pnomenusa* sp. Nov., *Pandoraea sputorum* sp. Nov. and *Pandoraea norimbergensis* comb. Nov., International Journal of Systematic and Evolutionary Microbiology, 50:887-899 (2000)).

Microbiological characteristics of the *Cryptococcus* sp. TMN-Y2 strain were examined and found to be as follows.
Form: produces a basidium as a sexual generation, exogeneously produces basidiospores thereon, and forms white colonies in many cases, which rapidly grow, are soft, and emit strong or blunt gloss. Bud-type conidia are mono-cellular, covered with a capsule, globular or oval, and multipolar.
Physiological characteristics: does not ferment sugar, but utilizes inositol and produces urease.
Growth range: Optimum growth temperature is 20 to 37° C.

These characteristics are the same as the characteristics of *Cryptococcus* sp. described in a published document (Takashima, M. and Nakase, T., Molecular phylogeny of the genus *Cryptococcus* and related species based on the sequence of 18S rDNA and internal transcribed spacer regions, Microbiol. Cult. Coll., 15, 35-47 (1999)).

Microbiological characteristics of the Trichosporon loubieri FF-Y2 strain were examined and found to be as follows.
Form: is sexually reproducible and produces ascospores in sporosacs. Colonies rapidly grow, have a smooth, wrinkled, torose, atrichosis to velvet surface, and emit strong or blunt gloss. Is wax-like and fragile, and has a white or a yellowish creamy color. Pseudomycelia and hyphae are abundant and well-developed. Bud-type conidia are mono-cellular and diverse in shape. Division-type conidia are mono-cellular and have an elongated form.
Physiological characteristics: is not fermented or only weakly fermented, and positive to sucrose, lactose, sorbitol, and glucose, and negative to laevulinate.
Growth range: Optimum growth temperature is 20 to 37° C.

These characteristics are the same as the characteristics of *Trichosporon* sp., which includes *Trichosporon loubieri*, reported in a published document (Wouter J. Middelhoven, Gloria Scorzetti and Jack W. Fell, *Trichosporon porosum* comb. nov., an anamorphic basidiomycetous yeast inhabiting soil, related to the *loubieri/laibachii* group of species that assimilate hemicelluloses and phenolic compounds, FEMS Yeast Research, Vol. 1, 15-22 (2001)).

Conditions suitable for mass culture of the microorganisms obtained above were examined to find that mass culture using a 10 L jar fermenter is suitable, with an optimum temperature being 28 to 30° C. and an optimum pH being 6.0 to 7.0.

The microorganisms of the present invention described above can be used independently or in combination of two or more for degrading estrogenic substances in wastewater or soil.

In order to degrade estrogenic substances in wastewater using the microorganism of the present invention, it is preferable to use the microorganism between the primary settling tank and the final settling tank in a wastewater treatment process, particularly in a secondary treatment step in a biological oxidation process. When the microorganism is used in the secondary treatment step, a system of attaching and growing the microorganism on a solid supporting-body surface is more preferable than a system of suspending the microorganism in a solution, because leakage of the microorganism can be prevented and a culture liquid with a higher concentration can be obtained by attaching the microorganisms to the surface of a solid supporting body. As the solid supporting body for attaching and growing the microorganism of the present invention, PVA (polyvinyl alcohol), porous cellulose, and the like can be given. Porous cellulose is preferred when used in the secondary treatment step. As the method for immobilizing the microorganism on a solid supporting body, a bonding-immobilization method using polypropylene, ceramic, and the like, an enclosing immobilization method such as the PVA-freezing method, and the like are given, with the bonding-immobilization method being preferable.

In the above-mentioned wastewater treatment, the microorganism of the present invention is used by directly supplying a culture broth, in which the cells have been grown to a concentration of $10^8$ to $10^9$ cells/mL by mass culture, to the wastewater treatment layer tank, or by supplying a carrier on which the microorganism has been immobilized to the treatment tank. The carrier on which the microorganism has been immobilized (immobilizing carrier) can be prepared by directly feeding a prescribed amount of carrier to a culturing vessel such as a jar fermenter or the like in which the microorganism has been mass-cultured and continuously operating the culturing vessel for two or three days while stirring to immobilize the microorganism. The immobilizing carrier is removed from the culture broth at the time of supplying to the treatment tank and fed to the treatment tank.

On the other hand, degradation of estrogenic substances in the soil using the microorganism of the present invention can be carried out by centrifuging the microorganism grown to a concentration of $10^8$ to $10^9$ cells/mL by mass culture in a jar fermenter, suspending the cells in a physiological saline solution or the like as required, and directly spreading the suspension over the contaminated soil to cause the microorganism to come in contact with the soil. In this case, the number of cells of the microorganism of the present invention to be spread over the surface or dug-up areas of the soil to be treated may be adjusted to about $10^9$ to $10^{10}$ cells/m$^3$.

In order to efficiently degrade estrogenic substances using the microorganism of the present invention, an apparatus equipped with a means for supporting the microorganism of the present invention and a means for causing the microorganism to come in contact with wastewater or soil can be used, for example. As specific examples of such an apparatus, bioreactors of an airlift-type, a column filling-type, or a lug flow-type can be given. Such an apparatus can also be used during the secondary treatment step of the wastewater treatment process to efficiently degrade estrogenic substances in wastewater or soil.

EXAMPLES

The present invention will be explained in more detail by examples which are not intended to be limiting of the present invention.

Example 1

Separation of Estrogenic Substance-Degrading Microorganism (1) Enrichment Culture The following MDG culture media 1 to 4 were filled into test tubes, each in an amount of 10 mL, and 17β-estradiol was added as an estrogenic substance to provide a concentration of 0.1%, to obtain groups of enrichment culture media, one group consisting of four media. 1 mL of activated sludge or return sludge collected from each of the wastewater treating processes for Fushimi Wastewater Treatment Plant (indicated by F: Kyoto-shi, Kyoto), Tarumi Wastewater Treatment Plant (indicated by TM: Kobe-shi, Hyogo), Tamagawa-joryu Treatment Plant (indicated by TJ: Akishima-shi, Tokyo), Morigasaki Treatment Center (indicated by M: Ota-ku, Tokyo), Northern Second Wastewater Treatment Plant (indicated by H: Yokohama-shi, Kanagawa), Todoroki Environment Center (indicated by TO: Kawasaki-shi, Kanagawa), and the Tachikawa-Fujimi Treatment Plant (indicated by TA:

Tachikawa-shi, Tokyo) was added to each test tube to prepare 56 enrichment culture medium solutions. These enrichment culture medium solutions were shake-cultured at 28° C. for one week. After completion of incubation, 1 mL of the culture solution was extracted from the culture broth and added to a test tube together with 10 mL of fresh MDG medium, and shake-cultured for one week. This operation was repeated five times to continuously culture the microorganisms over five generations.

TABLE 3

|  | MDG Medium 1 | MDG Medium 2 | MDG Medium 3 | MDG Medium 4 |
|---|---|---|---|---|
| $K_2HPO_4$ (g/L) | 3.5 | 3.5 | 3.5 | 3.5 |
| $KH_2PO_4$ | 1.5 | 1.5 | 1.5 | 1.5 |
| $(NH_4)_2SO_4$ | 0.5 | 0.5 | 0.5 | 0.5 |
| NaCl | 0.5 | 0.5 | 0.5 | 0.5 |
| $MgSO_4 \cdot 7H_2O$ | 0.15 | 0.15 | 0.15 | 0.15 |
| Trace elements (mL/L) | 1.0 | 1.0 | 1.0 | 1.0 |
| Yeast extract | 0.005 | 0.005 | — | — |
| pH | 6.0 | 7.0 | 6.0 | 7.0 |

TABLE 4

| Trace element | |
|---|---|
| $NaHCO_3 \cdot 10H_2O$ | 2.0 |
| $MnSO_4 \cdot 4H_2O$ | 0.3 |
| $ZnSO_4 \cdot 7H_2O$ | 0.2 |
| $(NH_4)_7Mo_7O_{24} \cdot 4H_2O$ | 0.02 |
| $CuSO_4 \cdot 5H_2O$ | 0.1 |
| $CoCl_2 \cdot 6H_2O$ | 0.5 |
| $CaCl_2 \cdot 2H_2O$ | 0.05 |
| $FeSO_4 \cdot 7H_2O$ | 0.5 |

(2) Isolation and Primary Screening of Microorganism

After enrichment cultivation in (1) above, 100 μL of each of the culture solutions was placed in a petri dish containing an ISP culture medium (Difco 277010), $R_2A$ culture medium (Difco 218263), or YM culture medium (Difco 271120: all manufactured by Difco) to cultivate the microorganisms, in order to isolate single colonies into each slant.

4 g of yeast extract, 10 g of malt extract, and 4 g of dextrose were added to 1 L of the above ISP medium, and the mixture was adjusted to 7.2 pH. 0.5 g of yeast extract, 0.5 g of proteose peptone, 0.5 g of casamino acid, 0.5 g of dextrose, 0.5 g of soluble starch, 0.3 g of sodium pyruvate, 0.3 g of potassium diphosphate, and 0.05 g of magnesium sulfate were added to 1 L of the above $R_2A$ medium, and the mixture was adjusted to 7.2 pH. 3 g of yeast extract, 3 g of malt extract, 5 g of peptone, and 10 g of dextrose were added to 1 L of the above YM medium, and the mixture was adjusted to 6.2 pH.

In addition, along with isolation of microorganisms, the enrichment culture solution obtained in (1) above was analyzed by direct development on a thin-layer chromatograph (TLC) to select the culture broth which consumed the substrate 17β-estradiol (hereinafter referred to from time to time as "E2") (Primary screening) The TLC was operated under the following conditions.

(Chromatography Conditions)
TLC plate used: MERCK (No. 13727)
Developing solvent: ethanol-benzene (1:9)
Amount of developing solvent: 5 mL
Developing time: about 16 minutes/10 cm
Amount of sample: 5 μL
Coloring reagent: Potassium dichromate-sulfuric acid (when necessary)

The E2 degrading activity and isolated number of stocks when each enrichment culture solution was developed on TLC are shown in Tables 5 and 6.

The degrading activity was evaluated according to the following standard.

TABLE 5

| Plant from which sludge is collected (Abbreviation) | Type of sludge | pH of medium | Addition of yeast extract | Symbol | Degradation activity | Number of separated stocks | Total number of stocks |
|---|---|---|---|---|---|---|---|
| Fushimi Wastewater Treatment Plant (F) | Activated sludge | 7 | − | FA |  | 14 | 35  64 |
|  |  | 7 | + | FB |  | 13 |  |
|  |  | 6 | − | FE |  | 4 |  |
|  |  | 6 | + | FF | ◯ | 4 |  |
|  | Return sludge | 7 | − | FI |  | 12 | 29 |
|  |  | 7 | + | FJ |  | 6 |  |
|  |  | 6 | − | FM |  | 5 |  |
|  |  | 6 | + | FN |  | 6 |  |
| Tarumi Wastewater Treatment Plant (TM) | Activated sludge | 7 | − | TMA |  | 6 | 26  60 |
|  |  | 7 | + | TMB |  | 8 |  |
|  |  | 6 | − | TME |  | 5 |  |
|  |  | 6 | + | TMF |  | 7 |  |
|  | Return sludge | 7 | − | TMI | ◯ | 12 | 34 |
|  |  | 7 | + | TMJ | ◯ | 13 |  |
|  |  | 6 | − | TMM | Δ | 4 |  |
|  |  | 6 | + | TMN | ◯ | 5 |  |
| Tamagawa-joryu Treatment Plant (TJ) | Activated sludge | 7 | − | TJA |  | 5 | 21  49 |
|  |  | 7 | + | TJB |  | 8 |  |
|  |  | 6 | − | THE |  | 6 |  |
|  |  | 6 | + | TJF |  | 2 |  |
|  | Return sludge | 7 | − | TJI |  | 11 | 28 |
|  |  | 7 | + | TJJ |  | 9 |  |
|  |  | 6 | − | TJM |  | 4 |  |
|  |  | 6 | + | TJN |  | 4 |  |
| Morigasaki Treatment Center (M) | Activated sludge | 7 | − | MA |  | 14 | 32  59 |
|  |  | 7 | + | MB |  | 9 |  |
|  |  | 6 | − | ME |  | 3 |  |
|  |  | 6 | + | MF |  | 6 |  |

TABLE 5-continued

| | | | | | | |
|---|---|---|---|---|---|---|
| Returned sludge | 7 | − | MI | | 7 | 27 |
| | 7 | + | MJ | | 11 | |
| | 6 | − | MM | ○ | 3 | |
| | 6 | + | MN | | 6 | |

(Evaluation)
○: Strong degrading activity
Δ: Comparatively strong degrading activity
Blank: No degrading activity (Content)
(no E2 spots)
(presence of very thin E2 spots)
(presence of E2 spots)

TABLE 6

| Plant from which sludge is collected (Abbreviation) | Type of sludge | pH of medium | Addition of yeast extract | Symbol | Degradation activity | Number of separated stocks | Total number of stocks |
|---|---|---|---|---|---|---|---|
| Northern Second Wastewater Treatment Plant (H) | Activated sludge | 7 | − | HA | | 7 | 25 | 53 |
| | | 7 | + | HB | | 9 | |
| | | 6 | − | HE | | 3 | |
| | | 6 | + | HF | | 6 | |
| | Return sludge | 7 | − | HI | | 8 | 28 |
| | | 7 | + | HJ | | 10 | |
| | | 6 | − | HM | | 3 | |
| | | 6 | + | HN | | 7 | |
| Todoroki Environment Center (TO) | Activated sludge | 7 | − | TOA | o | 12 | 35 | 67 |
| | | 7 | + | TOB | | 14 | |
| | | 6 | − | TOE | | 5 | |
| | | 6 | + | TOF | | 4 | |
| | Return sludge | 7 | − | TOI | o | 12 | 32 |
| | | 7 | + | TOJ | | 10 | |
| | | 6 | − | TOM | | 3 | |
| | | 6 | + | TON | o | 7 | |
| Tachikawa-Fujimi Treatment Plant (TA) | Activated sludge | 7 | − | TAA | Δ | 14 | 35 | 67 |
| | | 7 | + | TAB | | 13 | |
| | | 6 | − | TAE | | 6 | |
| | | 6 | + | TAF | | 2 | |
| | Return sludge | 7 | − | TAI | o | 14 | 32 |
| | | 7 | + | TAJ | o | 11 | |
| | | 6 | − | TAM | | 4 | |
| | | 6 | + | TAN | | 3 | |

As a result of the primary screening, it was found that the 17β-estradiol in the enrichment culture solutions of FF, TMI, TMJ, TMM, TMN, MM, TOA, TOI, TON, TAA, TAI, and TAJ was degraded, and a total of 111 stocks separated from the enrichment culture solutions were selected.

(3) Secondary Screening

The 111 stocks selected in the primary screening of (2) above were cultivated using 17β-estradiol as a substrate to select strains which produce a culture broth containing only a small amount of residual 17β-estradiol according to the following procedure.

The 111 microorganism stocks were cultivated by streak culture using a YM agar plate. A loopful amount of the culture broth was inoculated in each culture solution to which 17β-estradiol was added to provide a concentration of 100 mg/L. After one day, the total amount of the grown culture broth was extracted by a C18 solid-phase column (manufactured by Waters) and spotted onto TLC to select 23 microorganisms in which 17β-estradiol has been completely degraded.

(4) Ternary Screening

In order to select stocks which can degrade 17β-estradiol more rapidly and to examine their capability in degrading other natural estrogenic substances (estrone, estriol), the following experiment was carried out using the 23 stocks selected in the secondary screening of (3) above.

The 23 microorganism stocks were cultivated by streak culture using a YM agar plate, followed by cultivation using test tubes in the same manner as in the primary screening. The cultivation was terminated at 0, 3, 5, 8, or 24 hours after initiation, immediately followed by solid-phase extraction. Next, the total amount of the culture broth was retained in a C18 solid-phase column (manufactured by Waters), followed by elution with methanol. A surrogate substance (17β-estradiol-$d_4$) was added to an appropriate amount of the eluate. The mixture was dried to a solid state by a nitrogen stream and reacted with BSTFA (N,O-bis(trimethylsilyl)trifluoroacetamide) to induce a trimethylsilyllated compound (TMS compound). After drying again to a solid state by a nitrogen stream, the solid was dissolved in n-hexane and the sample solution was analyzed using a gas chromatography mass spectrometer (GC-MS). The concentration of estrogenic substances after cultivation for different periods of time was measured to determine the degraded amount. The conditions of GC-MS analysis are shown in Table 7.

TABLE 7

| | |
|---|---|
| GC | Agilent 6890 |
| Column | HP-5 (30 m × 0.32 mm i.d., 0.25 μm film thickness, Agilent) |
| Carrier gas | He, 1.5 mL/min |
| Oven temp. | 150° C. (2 min) → 50° C./min → 250° C. → 5° C./min → 300° C. (15 min) |
| Injection method | Splitless (1 min for purge-off time) |
| Injection volume | 1 μL |

TABLE 7-continued

| | |
|---|---|
| Injector temp. | 280° C. |
| Interface temp. | 300° C. |
| MS | JEOL JMS-700 |
| Mass resolution | 1000 |
| Detecter voltage | 1.0 kV |
| Operation mode | SIM |
| Monitoring ion | TMS-17β-Estradiol 416 (m/z) |
| | TMS-Estrone 342 (m/z) |
| | TMS-Estriol 504 (m/z) |
| | TMS-17β-Estradiol d$_4$ 420 (m/z) |
| Sampling rate | 50 (ms) |

Figure 1:
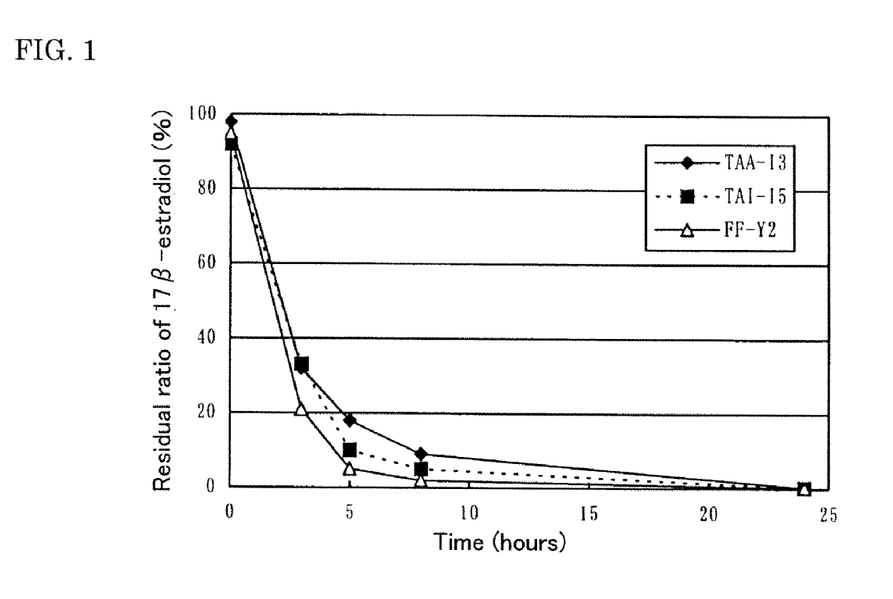
FIG. 1 is a drawing showing the change in the residual amount of 17β-estradiol over time.
Figure 2:
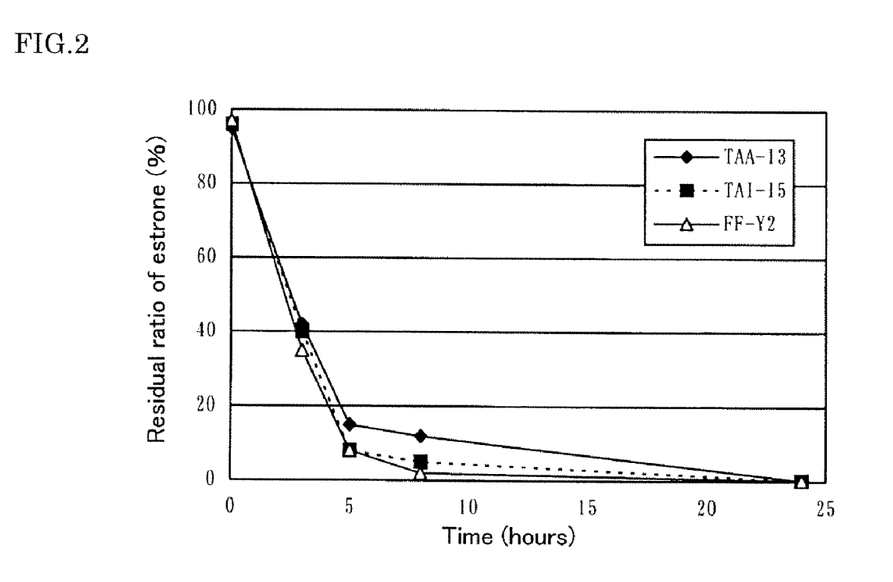
FIG. 2 is a drawing showing the change in the residual amount of estrone over time.
Figure 3:
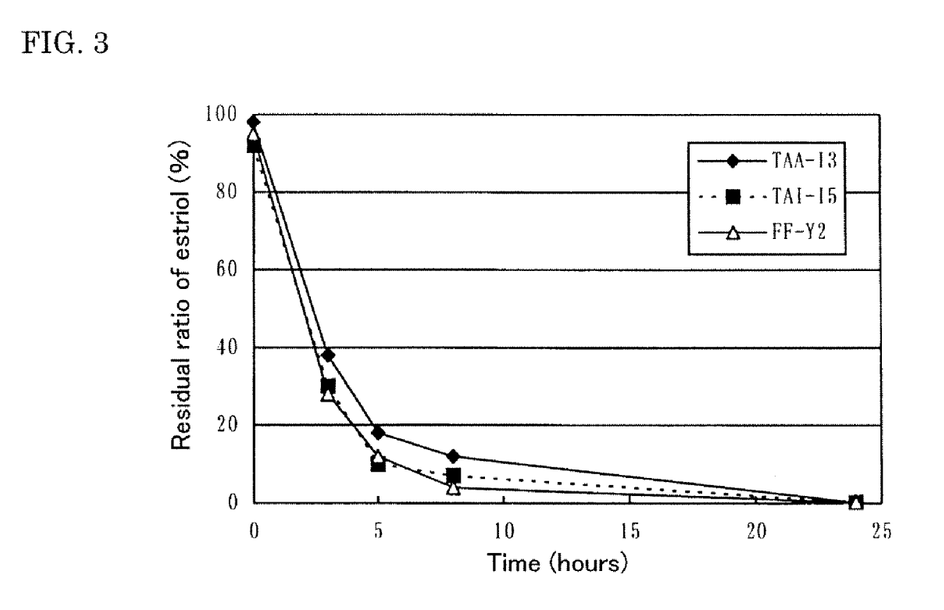
FIG. 3 is a drawing showing the change in the residual amount of estriol over time.
Figure 4:
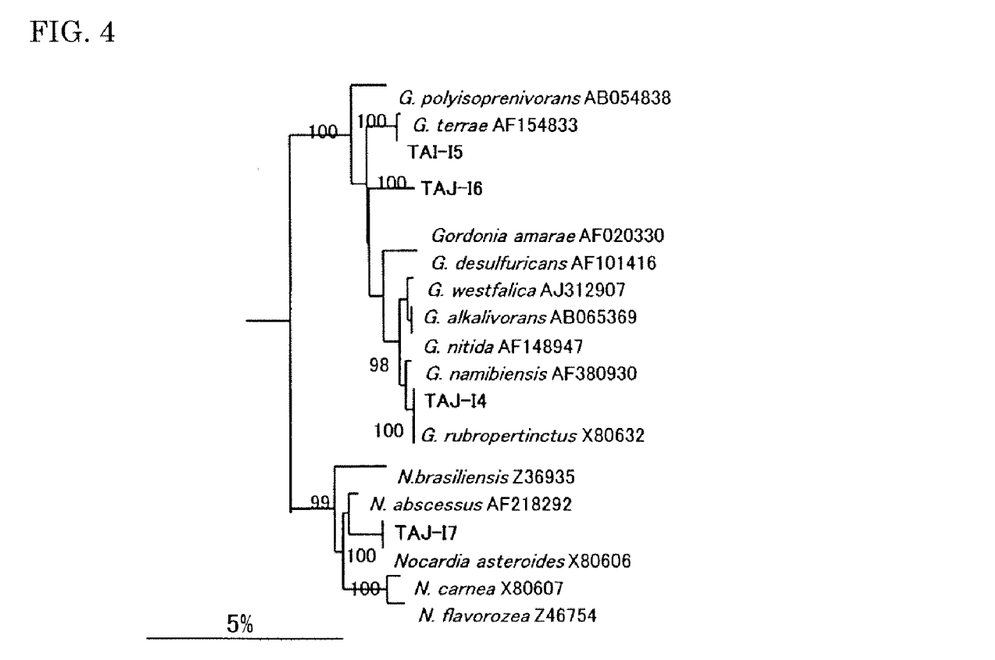
FIG. 4 shows a phylogenetic tree of the separated strain and the strain belonging to a gram-positive High G+C group closely related to the separated strain, prepared based on their 16S rDNA base sequences (about 1450 bases) using the neighbor-joining method (the numbers indicate Bootstrap values obtained by 100 times repetition and a bar at the lower left end indicates a 5% base substitution distance).
Figure 5:
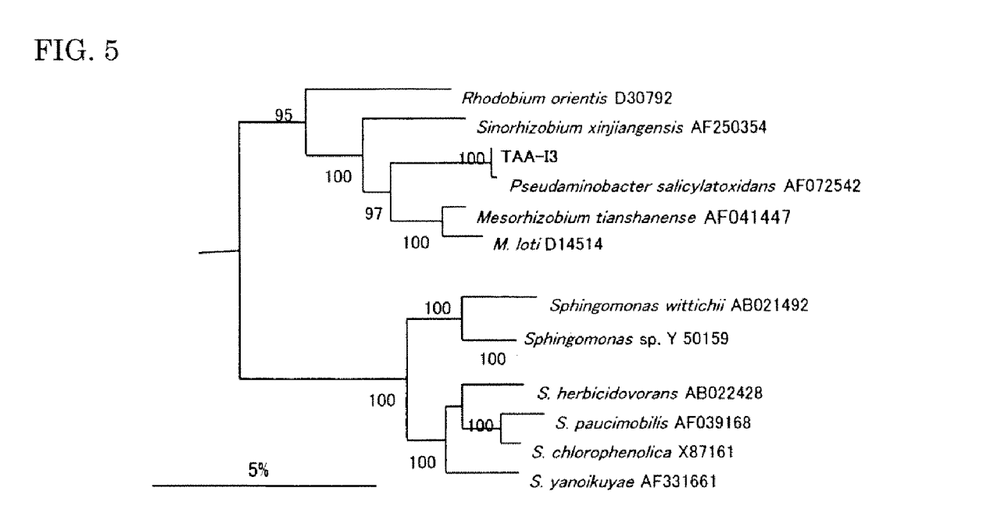
FIG. 5 shows a phylogenetic tree of the separated strain and the strain belonging to the Proteobacteria α-subdivision closely related to the separated strain, prepared based on their 16S rDNA base sequences (about 1450 bases) using the neighbor-joining method (the numbers indicate Bootstrap values obtained by 100 times repetition, and a bar at the lower left end indicates a 5% base substitution distance).
Figure 6:
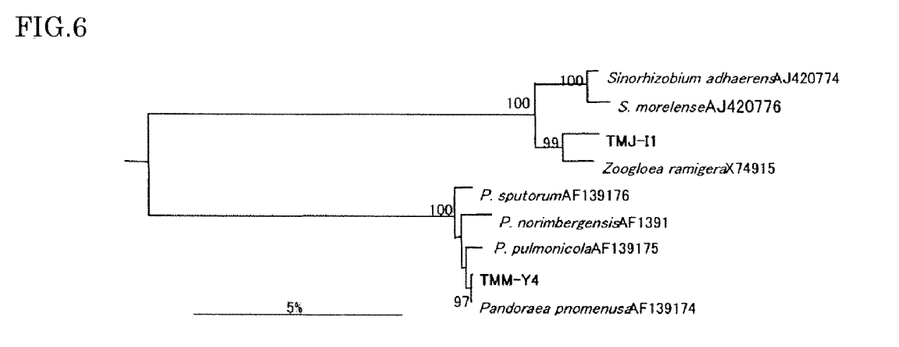
FIG. 6 shows a phylogenetic tree of the separated strain and the strain belonging to the Proteobacteria β-subdivision closely related to the separated strain, prepared based on their 16S rDNA base sequences (about 1450 bases) using the neighbor-joining method (the numbers indicate Bootstrap values obtained by 100 times repetition, and a bar at the lower left end indicates a 5% base substitution distance).
Figure 7:
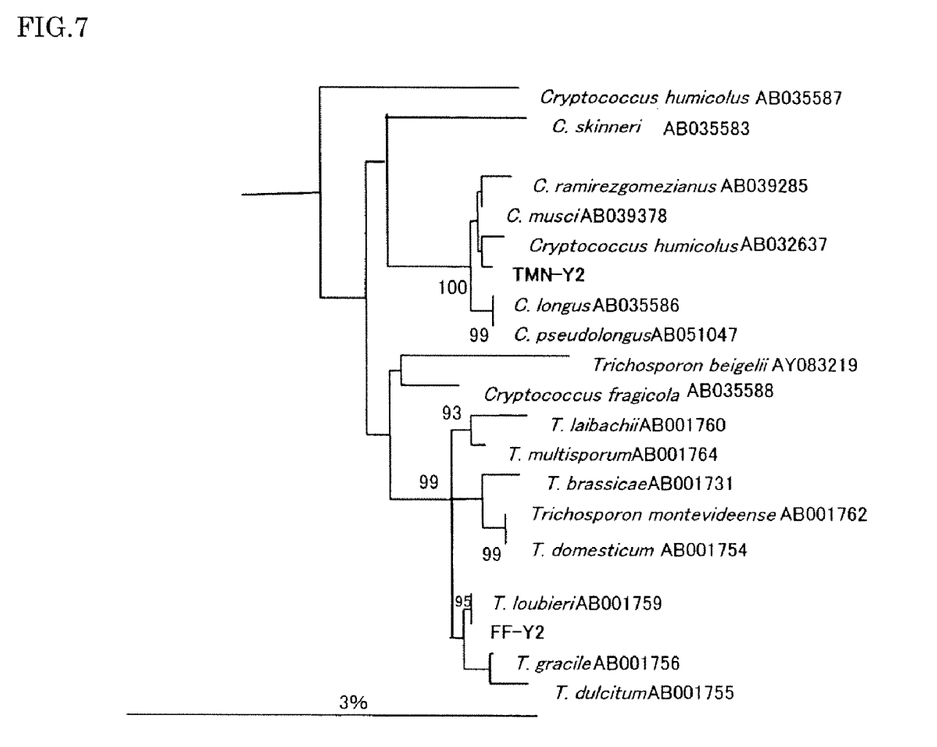
FIG. 7 shows a phylogenetic tree of the separated strain and yeast closely relative to the separated strain, prepared based on their 18S rDNA base sequences (about 1750 bases) using the neighbor-joining method (the numbers indicate Bootstrap values obtained by 100 times repetition and a bar at the lower left end indicates a 3% base substitution distance).

As a result of the screening, nine stocks which can degrade 65% or more of 17β-estradiol in five hours were selected. The changes over time of the residual amounts of 17β-estradiol, estrone, and estriol after degradation by the TAA-I3 strain, TAI-I5 strain, and FF-Y2 strain among the selected microorganisms are shown in FIG. 1 to FIG. 3, and the residual ratio (%) of each estrogen substance after five hours in solutions treated with each of nine strains is shown in Table 8.

TABLE 8

| | Time after start of experiment | 17β-estradiol (E2) | Estrone (E1) | Estriol (E3) |
|---|---|---|---|---|
| TAA-I3 | 5 h | 18% | 15% | 18% |
| TAI-I5 | 5 h | 10% | 8% | 10% |
| TAJ-I4 | 5 h | 24% | 32% | 22% |
| TAJ-I6 | 5 h | 33% | 28% | 35% |
| TAJ-I7 | 5 h | 20% | 22% | 20% |
| TMJ-I1 | 5 h | 15% | 10% | 16% |
| TMM-Y4 | 5 h | 15% | 42% | 55% |
| TMN-Y2 | 5 h | 18% | 20% | 17% |
| FF-Y2 | 5 h | 5% | 8% | 12% |

Example 2

Identification of Microorganisms Having Capability of Degrading Estrogen Substance (1) Identification of Strain Using 16S rDNA Sequence A phylogenetic tree was prepared using the 16S or 18S rDNA sequence for nine stocks of estrogenic substance-degrading microorganisms which were selected by the ternary screening according to the following procedure to conduct strain identification.

(a) DNA Extraction from Microorganism

DNA was extracted using the benzyl chloride method from each of the pure culture microorganisms of the above nine strains. The microorganisms were cultured using YM slope agar medium at 30° C. for three days. 250 μL of a DNA extract buffer solution (100 mmol/L Tris-HCl, 40 mmol/L EDTA, 9.0 pH), 200 μL of benzyl chloride, and 50 μL of 10% SDS were added to each of the collected microorganisms, and the mixture was vigorously shaken at 50° C. for 30 minutes. After adding 150 μL of 3 mol/L sodium acetate, the mixture was centrifuged and the supernatant liquid was transferred to a separate tube, followed by isopropanol precipitation, washing with 70% ethanol, and drying in air. The resulting solid was dissolved in 100 μL of TE buffer solution (10 mmol/L Tris-HCl (8.0 pH), 1 mmol/L EDTA).

(b) 16S or 18S rDNA Amplification PCR Reaction

The following 8F and 15R were used as amplification primers of 16S, and Y1F and Y1770R were used as amplification primers of 18S. A total 50 L of a reaction solution containing 10 mmol/L Tris-HCl (8.3 pH), 50 mmol/L KCl, 1.5 mmol/L MgCl$_2$, 200 μL of a dNTP mixture, 1 U of Taq DNA polymerase (manufactured by TAKARA Co., Ltd.), 50 ng of template DNA, and 0.4 μmol/L amplification primer was subjected to a 25 cycle PCR reaction using a DNA thermal cycler PTC200 (manufactured by MJ Research), one cycle consisting of a reaction for 20 seconds at 94° C., 15 seconds at 55° C., and 180 seconds at 72° C. The amplification product was purified using Microcon-PCR (manufactured by Millipore).

<Amplification Primers>

| | |
|---|---|
| 8F: | (5'-AGAGTTTGATCMTGGCTCAG-3') (SEQ ID NO: 1) |
| 15R: | (5'-AAGGAGGTGATCCARCCGCA-3') (SEQ ID NO: 2) |
| Y1F: | (5'-TATCTGGTTGATCCTGCCAGT-3') (SEQ ID NO: 3) |
| Y1770R: | (5'-CTACGGAAACCTTGTTACGAC-3') (SEQ ID NO: 4) |

(c) Determination of 16S or 18S rDNA Sequence 16S or 18S rDNA base sequence was decoded by ABI PRISM 373A sequencer (manufactured by ABI) using ABI PRISM™ Dye Terminator Kit (manufactured by Perkin Elmer). Primers used for decoding 16S and 18S rDNA are shown in Table 9. Auto Assembler™ (manufactured by Perkin Elmer) was used for sequence alignment.

TABLE 9

| Primer No. | Sequence (5' . . . 3') |
|---|---|
| (SEQ ID NOS: 1,5-10,2,3,11-18 and 4, respectively, in order of appearance) | |
| (For 16S) | |
| 8F | AGAGTTTGATCMTGGCTCAG |
| 520F | CAGGAGTGCCAGCAGCCGCGG |
| 930F | CAAGCGGTGGAGCATGTGG |
| 1100F | CAGGAGCAACGAGCGCAACCC |
| 520R | ACCGCGGCTGCTGGC |
| 800R | GGACTACCAGGGTATCTAAT |
| 1100R | AGGGTTGCGCTCGTTG |
| 15R | AAGGAGGTGATCCARCCGCA |
| (For 18S) | |
| Y1F | TATCTGGTTGATGCTGCCAGT |
| Y380F | CCGGAGAGGGAGCCTGAG |
| Y430R | TTTGCGCGCCTGCTGCCTT |
| Y570F | AGCCGCGGTAATTCCAGC |
| Y820R | CGTCCTATTCTATTATTCCATGC |
| Y970F | AAGAACGAAAGTTAGGGGATC |
| Y1200R | CTTTCCCCGTGTTGAGTCAA |
| Y1430F | AGGTCTGTGATGCCCTTAGA |
| Y1580R | CGCTTACTAGGAATTCCTCGTT |
| Y1770R | CTACGGAAACCTTGTTACGAC |

(d) Phylogenetic Analysis of 16S or 18S rDNA Sequence

Molecular evolution phylogenetic analysis was conducted using a phylogenetic analysis software program (Clustal X) using the 16S or 18S rDNA sequence obtained above and 16S rDNA base sequence of related bacteria obtained from a gene database such as DDBJ.

(e) Identification Results

The sequences were determined using the 18S rDNA sequence for the strains which were considered to be yeast from the bacillus form, and using the 16S rDNA sequence for other strains. The homology search of the determined sequence with the sequence on the database was conducted to find that, among the separated 23 strains, four strains belong to the gram-positive High G+C group, one strain belongs to α-Proteobacteria, two strains belong to β-Proteobacteria, and two strains are yeasts (FIG. 10). A phylogenetic tree was prepared for each group (FIG. 4 to FIG. 7).

TABLE 10

| Plant for which sludge is collected | | Separated microorganism No. | Result of identification | Higher classifycation group |
|---|---|---|---|---|
| Tachikawa-Fujimi Treatment Plant | Activated sludge | TAA-I3 | *Pseudaminobacter salicylatoxidans* | α |
| | Return sludge | TAI-I5 | *Gordonia terrae* | H |
| | | TAJ-I4 | *Gordonia rubropertinctus* | H |
| | | TAJ-I6 | *Gordonia amarae* | H |
| | | TAJ-I7 | *Nocardia asteroides* | H |
| Tarumi Wastewater Treatment Plant | Return sludge | TMJ-I1 | *Zoogloea* sp. | β |
| | | TMM-Y4 | *Pandoraea pnomenusa* | β |
| | | TMN-Y2 | *Cryptococcus* sp. | Y |
| Fushimi Wastewater Treatment Plant | Activated sludge | FF-Y2 | *Trichosporon loubieri* | Y | a: Proteobacteria a-subdivision
β: Proteobacteria β-subdivision
H: Gram positive High G + C bacteria
Y: Yeast Example 3

Degradation of Estrogenic Substance Using Activated Sludge

Raw activated sludge was obtained from an actually operating sewage disposal plant to measure the activity of *Gordonia terrae* TAI-I5 strain, which is regarded to exhibit strong estrogenic substance-degrading activity and to have a comparatively high level of safety.

(1) Selection of Microorganism Immobilizing Carrier

Commercially available microorganism immobilizing carriers were obtained to examine how the TAI-I5 strain adheres to each carrier. Polypropylene, ceramic, alumina-silica, and poly(vinyl alcohol) fixed activated carbon were used as the material of the immobilizing carrier. First, the microorganism of the TAI-I5 strain was mass-cultured in a jar fermenter to a concentration of $10^7$ cells/mL. Then, the above carriers, each in an amount of about 150 g, were added to 1 L of the culture solution, followed by shaking for 24 hours to immobilize the TAI-I5 strain on each of the carriers. After 24 hours, the carriers were removed and, after removing water using a filter paper, their weight was measured. Next, the carriers were put into a physiological saline solution, sufficiently stirred using a vortex mixer, and ultrasonically treated for five minutes to cause the TAI-I5 strain to be eluted from the carriers. This eluate was appropriately diluted with a physiological saline solution and applied to an agar medium (petri dish) prepared from an YG culture medium (Table 11) to incubate at 28° C. The number of living cells per unit weight of the carriers was measured. The results are shown in Table 12.

TABLE 11

| Component | Amount |
|---|---|
| D (+)-Glucose | 10 g/L |
| Polypepton | 5.0 g/L |
| Yeast Extract | 5.0 g/L |
| K$_2$HPO$_4$ | 2.0 g/L |
| KH$_2$PO$_4$ | 1.0 g/L |
| MgSO$_4$•7H$_2$O | 0.5 g/L |
| pH | 7.0 |

TABLE 12

| Material | Size (mm) | Specific gravity | Living cells (cells/g) |
|---|---|---|---|
| Polypropylene | φ4 | 0.98 | $1.2 \times 10^9$ |
| Ceramic | φ6 | >1 | $7.8 \times 10^6$ |
| Alumina-silica | φ12 | >1 | $2.2 \times 10^6$ |
| PVA immobilizing activated carbon | φ10 | >1 | $6.6 \times 10^8$ |

As a result of the immobilizing test, the carrier made of polypropylene was found to best immobilize the TAI-I5 strain among the commercially available carriers.

(2) Efficacy Test Using Microorganism Immobilizing Carrier

A polypropylene carrier with the TAI-I5 strain immobilized thereon was prepared in the same manner as in (1) above, and its 17β-estradiol-degrading activity was examined using activated sludge from a disposal plant which is actually operated in Ibaraki Prefecture.

The polypropylene carrier was sterilized at 121° C. for 10 minutes and charged to a solution of the TAI-I5 strain, cultured to a concentration of $10^7$ cells/mL, in an amount of 150 g/L. The mixture was incubated for 24 hours while shaking to immobilize TAI-I5 strain microorganisms onto the polypropylene carrier. The resulting microorganism immobilizing carrier was added to a aeration tank in an amount of 50 g per 1 L of sludge.

17β-estradiol was added to the sludge tank containing the polypropylene carrier to provide a 17β-estradiol concentration of 0.1 mg/L, and the concentration after eight hours was measured. The results are shown in Table 13. The concentration after eight hours indicates that almost 100% of the added 17β-estradiol was degraded.

TABLE 13

| Experiment No. | Initial concentration mg/L | Concentration after eight hours μg/L | Removal rate (%) |
|---|---|---|---|
| 1 | 0.098 | 0.15 | 99.8 |
| 2 | 0.10 | 0.082 | 99.9 |
| 3 | 0.099 | 0.055 | 99.9 |
| 4 | 0.095 | 0.55 | 99.4 |
| 5 | 0.091 | 0.14 | 99.8 |

INDUSTRIAL APPLICABILITY

An estrogenic substance-degrading microorganism of the present invention can promptly and effectively degrade an estrogenic substance.

Therefore, the estrogenic substance contained in domestic wastewater, wastewater discharged from a livestock farm, or the like can be promptly and effectively degraded by using the microorganism.

The invention claimed is:

1. A biologically pure estrogenic substance-degrading microorganism which, when $10^7$ to $10^8$ cells/L of the microorganism are caused to act on an estrogenic substance selected from the group consisting of 17β-estradiol, estrone, and estriol at a concentration of 100 mg/L, is capable of degrading 80% or more of the estrogenic substance in five hours, wherein the microorganism is selected from the group consisting of *Pseudaminobacter salicylatoxidans* TAA-I3 strain (FERM ABP-10519), *Gordonia terrae* TAI-I5 strain (FERM ABP-10521), *Zoogloea* sp. TMJ-I1 strain (FERM ABP-10523), *Cryptococcus* sp. TMN-Y2 strain (FERM ABP-10525) and *Trichosporon loubieri* FF-Y2 strain (FERM ABP-10526).

2. The microorganism of claim 1 which is *Pseudaminobacter salicylatoxidans* TAA-I3 strain (FERM ABP-10519).

3. The microorganism of claim 1, which is *Gordonia terrae* TAI-I5 strain (FERM ABP-10521).

4. The microorganism of claim 1, which is *Zoogloea* sp. TMJ-I1 strain (FERM ABP-10523).

5. The microorganism of claim 1, which is *Cryptococcus* sp. TMN-Y2 strain (FERM ABP-10525).

6. The microorganism of claim 1, which is *Trichosporon loubieri* FF-Y2 strain (FERM ABP-10526).

7. A method of biologically degrading an estrogenic substance, comprising contacting the estrogenic substance-degrading microorganism of claim 1 with an estrogenic substance selected from the group consisting of 17β-estradiol, estrone, and estriol.

8. The method according to claim 7, wherein the estrogenic substance is contained in wastewater or soil.

9. The method according to claim 7, wherein the estrogenic substance-degrading microorganism is attached and grown on a solid supporting-body surface selected from PVA (polyvinyl alcohol) and porous cellulose by a bonding-immobilization method or an enclosing immobilization method.

10. The method according to claim 8, wherein the estrogenic substance-degrading microorganism is attached and grown on a solid supporting-body surface selected from PVA (polyvinyl alcohol) and porous cellulose by a bonding-immobilization method or an enclosing immobilization method.

11. An apparatus for degrading an estrogenic substance comprising a means for supporting an estrogenic substance-degrading microorganism according to claim 1 and a means for causing the microorganism to come in contact with wastewater or soil.

\* \* \* \* \*